United States Patent
Olwill et al.

(10) Patent No.: US 10,064,963 B2
(45) Date of Patent: Sep. 4, 2018

(54) METHODS AND COMPOSITIONS FOR TREATING DISORDERS

(71) Applicant: PIERIS AG, Freising-Weihenstephan (DE)

(72) Inventors: Shane Olwill, Friesing-Weihenstephan (DE); Hendrik Gille, Munich (DE); Laurent Audoly, Mahwah, NJ (US); Marlon Hinner, Munich (DE); Elisabeth De Vries, Groningen (NL); Anton G. T. Terwisscha Van Scheltinga, Groningen (NL)

(73) Assignee: PIERIS PHARMACEUTICALS GMBH, Freising (DE)

( * ) Notice: Subject to any disclaimer, the term of this patent is extended or adjusted under 35 U.S.C. 154(b) by 496 days.

(21) Appl. No.: 14/369,353

(22) PCT Filed: Jan. 7, 2013

(86) PCT No.: PCT/EP2013/050158
§ 371 (c)(1),
(2) Date: Jun. 27, 2014

(87) PCT Pub. No.: WO2013/104586
PCT Pub. Date: Jul. 18, 2013

(65) Prior Publication Data
US 2015/0004098 A1    Jan. 1, 2015

Related U.S. Application Data

(60) Provisional application No. 61/584,355, filed on Jan. 9, 2012, provisional application No. 61/618,050, filed on Mar. 30, 2012.

(51) Int. Cl.
*A61K 51/00* (2006.01)
*A61M 36/14* (2006.01)
*A61K 51/08* (2006.01)

(52) U.S. Cl.
CPC .................................. *A61K 51/08* (2013.01)

(58) Field of Classification Search
CPC ...... A61K 51/00; A61K 51/08; A61K 51/088; A61K 2123/00; A61K 2121/00; A61K 38/00; A61K 39/00; C07K 2319/00; C07K 7/06; C07K 7/02; C07K 7/64; C07K 11/00; C07K 7/08; C07K 14/705; C07K 14/47
USPC .... 424/1.11, 1.65, 1.69, 9.1, 9.2; 514/1, 1.1, 514/19.2, 19.3, 19.4, 19.5, 21.2; 530/300, 530/350
See application file for complete search history.

(56) References Cited

U.S. PATENT DOCUMENTS

| | | | |
|---|---|---|---|
| 2007/0117145 A1* | 5/2007 | Meritet | G01N 33/6866 435/6.1 |
| 2009/0274623 A1 | 11/2009 | Smith et al. | |
| 2011/0098211 A1* | 4/2011 | Matschiner | C07K 14/47 514/1.2 |
| 2015/0252097 A1* | 9/2015 | Camphausen | C07K 14/78 424/134.1 |

FOREIGN PATENT DOCUMENTS

| | | |
|---|---|---|
| JP | 2009-292815 | 12/2009 |
| WO | WO 2090/095447 A1 | 8/2009 |
| WO | WO 2011/015634 A2 | 2/2011 |
| WO | WO 2012/136685 A1 | 10/2012 |

OTHER PUBLICATIONS

Decision of Rejection for Japanese Patent Application No. 2014-550714 dated Jun. 21, 2017. 4 pages.
Decision of Rejection for Japanese Patent Application No. 2014-550714 dated Jun. 21, 2017. 4 pages. English Translation.

* cited by examiner

*Primary Examiner* — D L Jones
(74) *Attorney, Agent, or Firm* — Foley & Lardner LLP

(57) ABSTRACT

The present disclosure relates to a method of treating, ameliorating or preventing a disorder by blocking the signaling pathway of c-Met, wherein said method comprises the step of administering a therapeutically effective amount of a composition to a subject in need thereof, which composition contains a lipocalin mutein or a fragment or a variant thereof. In addition, the present disclosure relates to a diagnostic composition suitable for use in, e.g., an immuno-imaging technique to detect the presence of c-Met as well as the uses thereof.

8 Claims, 7 Drawing Sheets
Specification includes a Sequence Listing.

a.

b.

c.

d.

a b

METHODS AND COMPOSITIONS FOR TREATING DISORDERS

CROSS-REFERENCE TO RELATED APPLICATIONS

This application is a National Stage application of PCT/EP2013/050158, filed Jan. 7, 2013, which claims priority from U.S. Provisional Application Nos. 61/584,355, filed Jan. 9, 2012, and 61/618,050, filed Mar. 30, 2012.

SEQUENCE LISTING

The instant application contains a Sequence Listing which has been submitted electronically in ASCII format and is hereby incorporated by reference in its entirety. Said ASCII copy, created on Dec. 16, 2016, is named 029029_0153_SL.txt and is 4,564 bytes in size.

FIELD OF THE INVENTION

The present disclosure relates to a method of treating, ameliorating or preventing a disorder by blocking the signaling pathway of c-Met, wherein said method comprises the step of administering a therapeutically effective amount of a composition to a subject in need thereof, which composition contains a lipocalin mutein or a fragment or a variant thereof. In one aspect, the lipocalin mutein can block or contributes to blocking c-Met signalling that involves the binding of c-Met's ligand, HGF, to c-Met. In yet another aspect, however, the lipocalin mutein can also block or contributes to blocking c-Met signalling independent of the binding of HGF to c-Met. Accordingly, in addition to targeting ligand-dependent tumors, this approach can also impair ligand-independent activations of c-Met, for example, due to c-Met's overexpression or mutations of the intracellular domains. Moreover, this approach can be used to treat a disorder as a result of both HGF-involved c-Met signaling and c-Met signaling that is independent of the binding of HGF to c-Met. In addition, the present disclosure relates to a diagnostic composition suitable for use in, e.g., an immuno-imaging technique to detect the presence of c-Met as well as the uses thereof.

BACKGROUND

Proteins that selectively bind to selected targets by way of non-covalent interaction play a crucial role as reagents in biotechnology, medicine, bioanalytics as well as in the biological and life sciences in general. Antibodies, i.e. immunoglobulins, are a prominent example of this class of proteins. Despite the manifold needs for such proteins in conjunction with recognition, binding and/or separation of ligands/targets, what are currently used are almost exclusively immunoglobulins.

Additional proteinaceous binding molecules that have antibody-like functions are the members of the lipocalin family, which have naturally evolved to bind ligands. Lipocalins occur in many organisms, including vertebrates, insects, plants and bacteria. The members of the lipocalin protein family (Pervaiz, S., & Brew, K. (1987) FASEB J. 1, 209-214) are typically small, secreted proteins and have a single polypeptide chain. They are characterized by a range of different molecular-recognition properties: their ability to bind various, principally hydrophobic molecules (such as retinoids, fatty acids, cholesterols, prostaglandins, biliverdins, pheromones, tastants, and odorants), their binding to specific cell-surface receptors and their formation of macromolecular complexes. Although they have, in the past, been classified primarily as transport proteins, it is now clear that the lipocalins fulfill a variety of physiological functions. These include roles in retinol transport, olfaction, pheromone signalling, and the synthesis of prostaglandins. The lipocalins have also been implicated in the regulation of the immune response and the mediation of cell homoeostasis (reviewed, for example, in Flower, D. R. (1996) *Biochem. J.* 318, 1-14 and Flower, D. R. et al. (2000) *Biochim. Biophys. Acta* 1482, 9-24).

Lipocalins share unusually low levels of overall sequence conservation, often with sequence identities of less than 20%. In strong contrast, their overall folding pattern is highly conserved. The central part of the lipocalin structure consists of a single eight-stranded anti-parallel β-sheet closed back on it to form a continuously hydrogen-bonded β-barrel. This β-barrel forms a central cavity. One end of the barrel is sterically blocked by the N-terminal peptide segment that runs across its bottom as well as three peptide loops connecting the β-strands. The other end of the β-barrel is open to the solvent and encompasses a target-binding site, which is formed by four flexible peptide loops. It is this diversity of the loops in the otherwise rigid lipocalin scaffold that gives rise to a variety of different binding modes, each capable of accommodating targets of different size, shape, and chemical character (reviewed, e.g., in Flower, D. R. (1996), supra; Flower, D. R. et al. (2000), supra, or Skerra, A. (2000) *Biochim. Biophys. Acta* 1482, 337-350).

Various PCT publications (e.g., WO 99/16873, WO 00/75308, WO 03/029463, WO 03/029471 and WO 2005/19256) disclose how muteins of various lipocalins (e.g. human tear lipocalin) can be constructed to exhibit a high affinity and specificity against a target that is different than a natural ligand of a wild type lipocalin. This can be done, for example, by mutating one or more amino acid positions of at least one of the four peptide loops. In addition, PCT publication WO 2009/095447 teaches methods for generation of lipocalin muteins directed against c-Met.

Generally, kinases are enzymes known to regulate the majority of cellular pathways, especially pathways involved in signal transduction or the transmission of signals within a cell. Because protein kinases have profound effect on a cell, kinase activity is highly regulated. Kinases can be turned on or off by phosphorylation and by binding to activator proteins or inhibitor proteins. Deregulated kinase activity is a frequent cause of disease, particularly cancer where kinases regulate many aspect that control cell growth, movement and death. Many of these genetic defects have been identified as key components of signaling pathways responsible for proliferation and differentiation of cancers. Receptor tyrosine kinase (RTK) targeted agents such as trastuzumab, cetuximab, bevacizumab, imatinib and gefitinib inhibitors have illustrated the interest of targeting this protein class for treatment of selected cancers.

c-Met is the prototypic member of a sub-family of RTKs. The c-Met family is structurally different from other RTK families, and is the only known high-affinity receptor for hepatocyte growth factor (HGF), also called scater factor (SF) (D. P. Bottaro et al., Science 1991, 251: 802-804; L. Naldini et al., Eur. Mol. Biol. Org. J. 1991, 10:2867-2878). In this regard, HGF/SF is the ligand for the c-Met receptor, while c-Met is a receptor tyrosine kinase activated by HGF/SF (Seidel, C., Borset, M., Hjorth-Hansen, H., Sundan, Al., Waage, A., (1998) Role of Hepatocyte Growth Factor and Its Receptor c-Met in Multiple Myeloma Med Oncol 15, 145-53; Brset, M., Seidel, C., Hjorth-Hansen, H., Waage, A., Sundan, A. (1999) The Role of Hepatocyte Growth Factor and Its Receptor c-Met in Multiple Myeloma and Other Blood Malignancies Leukemia & Lymphoma 32, 249-256).

Multiple signaling pathways have been associated with the biological responses mediated by c-Met activation (Abounader, R., et al. (2001) Signaling Pathways in the Induction of c-Met Receptor Expression by its Ligand Scatter Factor/Hepatocyte Growth Factor in Human Glioblastoma, J. Neurochem, 75, 1497-1508). When HGF/SF activates c-Met, the latter in turn may activate a number of kinase pathways, including, but not limited to, the pathway from Ras to Raf to Mek to the mitogen-activated protein kinase ERK1 to the transcription factor ETS1. Co-expression of unaltered c-Met and HGF/SF, as well as activating mutations, are oncogenic (Abounader, R., et al. (2001) Signaling Pathways in the Induction of c-Met Receptor Expression by its Ligand Scatter Factor/Hepatocyte Growth Factor in Human Glioblastoma, J. Neurochem, 75, 1497-1508).

c-Met and HGF are both required for normal mammalian development and have been shown to be particularly important in cell migration, morphogenic differentiation, and organization of the three-dimensional tubular structures as well as growth and angiogenesis (F. Baldt et al., Nature 1995, 376:768-771; C. Schmidt et al., Nature. 1995, 373: 699-702; Tsarfaty et al., Science 1994, 263:98-101). While the controlled regulation of c-Met and HGF have been shown to be important in mammalian development, tissue maintenance and repair (Nagayama T, Nagayama M, Kohara S, Kamiguchi H, Shibuya M, Katoh Y, Itoh J, Shinohara Y., Brain Res. 2004, 5; 999(2):155-66; Tahara Y, Ido A, Yamamoto S, Miyata Y, Uto H, Hon T, Hayashi K, Tsubouchi H., J Pharmacol Exp Ther. 2003, 307(1):146-51), their dysregulation is implicated in the progression of cancers.

It also has been known in the art that c-Met plays a role in normal hematopoiesis, and is expressed in various lymphoid and leukemic cell lines. A wide variety of human tumors express both c-Met and HGF/SF and their expression contribute to the malignant progression of gliomas. In addition, overexpression of either HGF or c-Met is found in several cancers, and have been correlated with disease progression and clinical outcome (Ferracini, R., DiRenzo, M. F., Scotlandi, J., Baldini, N., Olivero, M., Lollini, P., Cremona, O., Campanacci, M., Comoglio, P. M. (1995) The Met/HGF Receptor Is Over-Expressed in Human Osteosarcomas and Is Activated By Either a Paracrine or an Autocrine Circuit Oncogene 10, 739-49; Rusciano, D., Lorenzoni, P., Burger, M. M. (1995) Expression of Constitutively Activated Hepatocyte Growth Factor/Scatter Factor Receptor (c-Met) in B16 Melanoma Cells Selected for Enhanced Liver Colonization Oncogene 11, 1979-87). Furthermore, c-Met has been implemented in the development and progression of colon cancer (Herynk, M. H., Stoeltzing, O., Reinmuth, N., Parikh, N. U., Abounader, R., Laterra, J., Radinsky, R., Ellis, L. M., Gallick, G. E. (2003) Down-Regulation of c-Met Inhibits Growth in the Liver of Human Colorectal Carcinoma Cells Cancer Res 63, 2990-6, prostate cancer, Kim, S. J., Johnson, M., Koterba, K., Herynk, M. H., Uehara, H., Gallick, G. E. (2003) Reduced c-Met Expression By an Adenovirus Expressing a c-Met Ribozyme Inhibits Tumorigenic Growth and Lymph Node Metastases of PC3-LN4 Prostate Tumor Cells in an Orthotopic Nude Mouse Model Clin Cancer Res 9, 5161-70), and cancer in other organs (Longati, P., Comoglio, P. M., Bardelli, A. (2001) Receptor Tyrosine Kinases as Therapeutic Targets: the Model of the MET Oncogene Curr Drug Targets 2, 41-55), as well in blood malignancies such as multiple myeloma (Brset, M., Seidel, C., Hjorth-Hansen, H., Waage, A., Sundan, A. (1999) The Role of Hepatocyte Growth Factor and Its Receptor c-Met in Multiple Myeloma and Other Blood Malignancies Leukemia & Lymphoma 32, 249-256). c-Met activation enhances cellular proliferation, migration, morphogenesis, survival (including protection from apoptosis), and protease synthesis, characteristics that are associated with invasive cell phenotype and poor clinical outcomes and drug resistance in cancer patients.

Inappropriate c-Met activation can arise, for example, by so-called ligand-dependent mechanisms (J. G. Christensen, Burrows J. and Salgia R., Cancer Latters. 2005, 226:1-26). In this sense, binding of HGF to c-Met can lead to receptor dimerization or multimerization, phosphorylation of multiple tyrosine residues in the intracellular region, catalytic activation, and downstream signaling. On the other hand, c-Met may also be activated via so-called ligand-independent mechanisms. This activation can be instigated by, for example, receptor over-expression and/or amplification, or paracrine or autocrine activation and/or mutation. In either case, the aberrant signaling pathway driven by inappropriate activation of c-Met is one of the most frequently dysregulated pathways in human cancers, occurs in virtually all types of solid tumors and plays a crucial role in tumorigenesis and metastasis (Birchmeier et al., Nat. Rev. Mol. Cell Biol. 2003, 4:915-925; L. Trusolino and Comoglio P. M., Nat Rev. Cancer. 2002, 2(4):289-300).

Various therapeutic approaches are aimed at the HGF/c-Met pathway. However, no therapeutic methods that possess the features attendant to the therapeutic methods provided by present disclosure have been previously described.

Moreover, with the overexpression and over-activation of c-Met in various cancers being linked to increased proliferation, progression to metastatic disease, and drug resistance (Peruzzi B, Bottaro D P: Targeting the c-met signaling pathway in cancer. *Clin Cancer Res* 2006, 12(15):3657-3660), the development of a lipocalin mutein that is suitable to assess, in vivo, changes in Met expression would improve the accuracy of diagnosis of c-Met-mediated disease and monitoring of responses to c-Met-targeted therapies.

The need is therefore felt for improved solutions enabling more reliable detection of cells expressing c-Met (e.g. tumorigenic cells), which is as convenient and economical as possible, and this disclosure provides such improved solutions.

DETAILED DESCRIPTION

Figure 1:
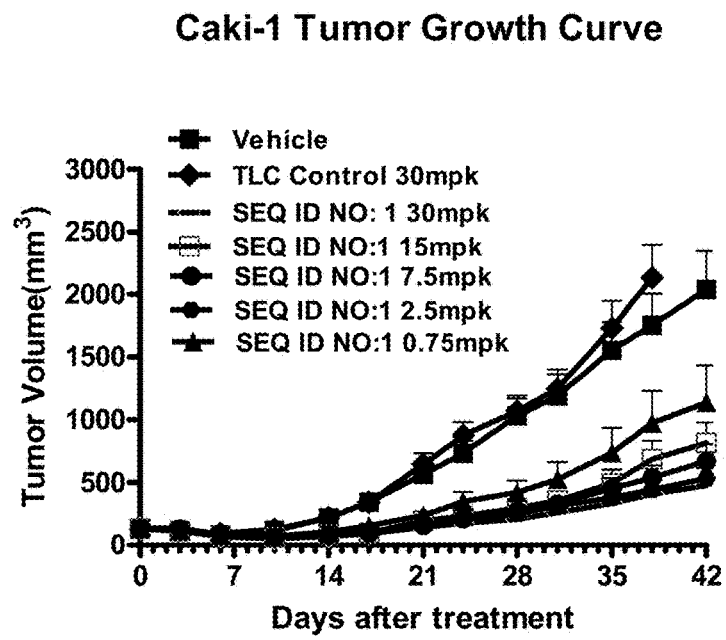
FIG. 1 shows the dose-dependent anti-tumor effect of a lipocalin mutein (SEQ ID NO: 1) linked to PEG40 in the Caki-1 xenograft tumor model. Nude mice bearing established tumors (average volume of 100-150 mm3) were separated into treatment groups (n=10) and received a daily intraperitoneal (i.p.) dose of the lipocalin mutein (SEQ ID NO: 1) or relevant control. All treatment groups receiving the lipocalin mutein (SEQ ID NO: 1) displayed statistically significantly tumor-growth inhibition compared to controls (P<0.01).

A. One or More Lipocalin Muteins of the Disclosure

In some embodiments, a lipocalin mutein described herein as included in a pharmaceutical or a diagnostic composition disclosed herein has a detectable binding affinity to c-Met or a domain or fragment thereof. The expression "detectable binding affinity" is meant that a lipocalin mutein of the disclosure binds c-Met with a dissociation constant of at least 200 nM or less. In some embodiments, a lipocalin mutein of the disclosure has a high affinity for c-Met or a domain or fragment thereof, for example, the lipocalin mutein is able to bind c-Met even if the expression levels of Met on the cell surface are very low. In some further embodiments, a lipocalin mutein of the disclosure binds c-Met with a dissociation constant for c-Met of at least 100, 20, 1 nM or even less. The binding affinity of a lipocalin mutein to c-Met can be measured by a multitude of methods such as fluorescence titration, competition ELISA or surface plasmon resonance (BIAcore).

In some further embodiments, a lipocalin mutein of the disclosure can be internalized, by itself and/or when fused to one or more half-life extending moieties, from the surface of cells expressing c-Met.

In one embodiment, a lipocalin mutein of the disclosure has tunable half-lives when fused to various half-life extending moieties of the disclosure. In some further embodiments, the lipocalin mutein is conjugated to a half-life extending moiety of the disclosure in order to yield a half-life of interest for a pharmaceutical or diagnostic composition of the disclosure. In one further embodiment, the half-life of interest is compatible with the time needed to achieve imaging results as visualized by a particular detectable signaling label of interest. In one further embodiment, the half-life of interest is practical and convenient for a patient in need thereof. The conjugation can be carried out using any conventional coupling method known in the art.

One or more diagnostic compositions of the disclosure are particularly attractive for this purpose, particularly because of the ability to internalize upon binding a c-Met molecule on a cell surface, which enables a good tumor to non-tumor ratio and consequently a surprising sensibility and specificity for the detection of tumorigenic cells. A diagnostic composition of the disclosure also is particularly attractive for use as an imaging agent because of a tunable half-life that is driven by the ability to easily fuse, conjugate or otherwise attach any of a range of half-life-extension moieties (such as a PEG) to the lipocalin mutein, thereby enabling the use of an optimal half-life-extension moiety. Having a the flexible residence time allows contacting between diagnostic compositions of the disclosure and c-Met for a period of time that is not only sufficient for the binding of c-Met and thus detecting of c-Met level, but also convenient and economical for patients, where the one or more diagnostic compositions of the disclosure can have a half-life compatible with the time needed to achieve imaging results (e.g. tumor-to-non-tumor ratios) as can be visualized by various detectable signaling labels. Moreover, the fact that one or more diagnostic compositions of the disclosure are able to be internalized within the tumorigenic cells A lipocalin mutein described herein may be a human tear lipocalin (hTLc; SEQ ID NO: 3) which has at any one amino acid at a position corresponding to position 26-34, 56-58, 80, 83, 104-106, and 108 of the linear polypeptide sequence of the mature human tear lipocalin (SEQ ID NO: 3) a mutated amino acid. The lipocalin mutein may further comprises (i) at least one of the amino acid substitutions of the linear polypeptide sequence of the mature human tear lipocalin selected from Cys 61→Ser, Cys 101→Ser and Cys 153→Ser, and/or (ii) at least one additional amino acid substitution of the linear polypeptide sequence of the mature human tear lipocalin selected from Arg 111→Pro and Lys 114→Trp. In a particularly preferred embodiment, the lipocalin mutein described herein may have at least 75% identity to the sequence of mature human tear lipocalin. Due to multiple rounds of randomized mutations or because of structure-function relationship, an amino acid residue of the wild type tear lipocalin sequence may also be retained in a lipocalin mutein of the disclosure.

In a particular embodiment, a lipocalin mutein of the disclosure is represented by SEQ ID NO: 1 or a variant thereof. Preferably, the variant has a sequence identity or homology of at least a 75%, 80%, 85%, 90% or 95% to the amino acid represented by SEQ ID NO: 1 or SEQ ID NO: 2.

The term "position" when used in accordance with the disclosure means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids. Accordingly, the position of a given amino acid in accordance with the disclosure which may be substituted may very due to deletion or addition of amino acids elsewhere in a (mutant or wild-type)

lipocalin. Similarly, the position of a given nucleotide in accordance with the present disclosure which may be substituted may very due to deletions or additional nucleotides elsewhere in a mutein or wild type lipocalin 5'-untranslated region (UTR) including the promoter and/or any other regulatory sequences or gene (including exons and introns).

Thus, under a "corresponding position" in accordance with the disclosure, it is preferably to be understood that nucleotides/amino acids may differ in the indicated number but may still have similar neighbouring nucleotides/amino acids. Said nucleotides/amino acids which may be exchanged, deleted or added are also comprised by the term "corresponding position". When used herein "at a position corresponding to a position" a position in a "query" amino acid (or nucleotide) sequence is meant that corresponds to a position in a "subject" amino acid (or nucleotide) sequence.

The term "fragment" as used in the present disclosure in connection with one or more muteins of the present disclosure relates to proteins or peptides derived from full-length mature human tear lipocalin that are N-terminally and/or C-terminally shortened, i.e. lacking at least one of the N-terminal and/or C-terminal amino acids. Such fragments comprise preferably at least 10, more preferably 20, most preferably 30 or more consecutive amino acids of the primary sequence of mature human tear lipocalin and are usually detectable in an immunoassay of mature human tear lipocalin.

The term "variant" as used in the present disclosure relates to derivatives of a protein or peptide that comprise modifications of the amino acid sequence, for example by substitution, deletion, insertion or chemical modification. Preferably, such modifications do not reduce the functionality of the protein or peptide. As an illustrative example, the first 4 N-terminal amino acid residues (HHLA) as well as the two last C-terminal amino acid residues (SD) can be deleted in a tear lipocalin mutein of the disclosure without affecting the biological function of the protein (e.g. SEQ ID NO: 1). Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

By "identity" or "sequence identity" as used in the present disclosure, it is meant a property of sequences that measures their similarity or relationship. The term "sequence identity" or "identity" as used in the present disclosure means the percentage of pair-wise identical residues—following (homologous) alignment of a sequence of a polypeptide of the disclosure (e.g., any lipocalin mutein of the disclosure or the mature human tear lipocalin (SEQ ID NO: 3) with a sequence in question—with respect to the number of residues in the longer of these two sequences. Percent identity is determined by dividing the number of identical residues by the total number of residues and multiplying the product by 100. The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g., any lipocalin mutein of the disclosure or the wide-type human tear lipocalin).

A lipocalin mutein that is homologous to the lipocalin mutein shown in SEQ ID No: 1 or 2 or to the mature human tear lipocalin mutein, fragment or variant thereof as disclosed herein has still the capability of block or contribute to blocking the signalling pathway of c-Met. Preferably, it can block or contribute to blocking c-Met signaling independent of the binding of HGF to c-Met in said subject. It is also preferred, that a homologous lipocalin mutein can be internalized from the surface of cells expressing c-Met upon binding to a c-Met molecule.

The percentage of sequence homology or sequence identity can, for example, be determined herein using the program BLASTP, version blastp 2.2.5 (Nov. 16, 2002; cf. Altschul, S. F. et al. (1997) Nucl. Acids Res. 25, 3389-3402). In this embodiment the percentage of homology is based on the alignment of the entire polypeptide sequences (matrix: BLOSUM 62; gap costs: 11.1; cutoff value set to 10-3 in a pairwise comparison, e.g. any of the lipocalin muteins shown in SEQ ID NO: 1 or 2 or the mature human tear lipocalin (SEQ ID NO: 3) can serve as reference. Homology or identity, respectively, is calculated as the percentage of numbers of "positives" (homologous amino acids) indicated as result in the BLASTP program output divided by the total number of amino acids selected by the program for the alignment.

B. One or More Pharmaceutical Compositions of the Disclosure and Uses Thereof

In another embodiment, the present disclosure relates to a method of treating, ameliorating or preventing a disorder by blocking the signaling pathway of c-Met, wherein said method comprises administering to a subject in need thereof a therapeutically effective amount of a pharmaceutical composition comprising a lipocalin mutein of the disclosure or fragments or variants thereof in the subject. In some further embodiments, a pharmaceutical composition of the disclosure can be internalized from the surface of cells expressing Met, upon binding to a c-Met molecule. Likewise, the present disclosure relates to a lipocalin mutein of the disclosure or fragments or variants thereof for use in a method of treating, ameliorating or preventing a disorder by blocking the signaling pathway of c-Met. Said method is intended to include administering to a subject in need thereof a therapeutically effective amount of a lipocalin mutein of the disclosure or fragments or variants thereof, said lipocalin mutein, fragments, or variants thereof are preferably in the form of a pharmaceutical composition. Generally, all methods of treatment, amelioration or prevention as described herein are convertible into the afore-used claim format.

A disorder that is preferably treated, ameliorated or prevented by said method is associated with a cell proliferative disorder or cancer.

In another aspect, the present disclosure teaches the use of a lipocalin mutein, or one of its functional fragments or derivatives, and/or of a composition as above described for the preparation of a medicament intended to inhibit the growth and/or the proliferation of tumor cells. Another aspect of the disclosure comprises the use of the lipocalin mutein, or one of its functional fragments or derivatives and/or of a composition as described above for the preparation of a medicament intended for the prevention or for the treatment of cancer.

As one preferred embodiment, the present disclosure also provides a method intended to inhibit the growth and/or the proliferation of tumor cells in a patient, wherein said method comprises the administration to a patient in need thereof of a lipocalin mutein, or one of its functional fragments or derivatives according to the disclosure.

The present disclosure further relates to a method for the prevention or the treatment of cancer in a patient in need thereof, wherein said method comprises the administration to the patient of a pharmaceutical composition provided herein containing a lipocalin mutein, or one of its functional fragments or derivatives according to the disclosure.

In a particular preferred aspect, said cancer is a cancer chosen from prostate cancer, osteosarcomas, lung cancer, breast cancer, endometrial cancer, glioblastoma or colon cancer.

As explained above, an advantage of the disclosure is to allow the treatment of HGF dependent and independent Met-activation related cancers.

In the present description, pharmaceutically acceptable vehicle is intended to indicate a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Preferably, these compounds can be administered by the systemic route, in particular, by the intravenous route, by the intramuscular, intradermal, intraperitoneal or by the oral route. In a more preferred manner, the composition comprising one or more lipocalin muteins according to the disclosure can be administered several times, in a sequential manner.

Modes of administration, dosages and optimum pharmaceutical forms can be determined according to the criteria generally taken into account in the establishment of a treatment adapted to a patient such as, for example, the age or the body weight of the patient, the seriousness of his/her general condition, the tolerance to the treatment and the secondary effects noted.

In various preferred embodiments, it is possible to attach a half-life altering (e.g., extending) moiety to a lipocalin mutein as comprised in a pharmaceutical composition of the disclosure, to alter the half-life and, therefore, pharmacokinetic profile, of the pharmaceutical composition. One way to do this is to mutate or add at least one amino acid residue in the lipocalin mutein that is capable of serving as a point of attachment for the half-life extending moiety. This can be, for example, the addition of or substitution to cysteine (e.g. in SEQ ID NO: 1 over SEQ ID NO: 2) to introduce a reactive group, for example, for the conjugation to other compounds, such as polyethylene glycol (PEG), hydroxyethyl starch (HES), biotin, peptides or proteins, or for the formation of non-naturally occurring disulphide linkages. In this regard, one or more lipocalin muteins provided for herein may be modified to alter its pharmacokinetic properties in a subject.

In various further embodiments, the PK properties such as half-life of a composition containing a lipocalin mutein can also be altered by a protein that, itself, extends the serum half-life of the mutein. The mutein can, for example, be conjugated or expressed as a fusion protein with a moiety selected from the group consisting of an Fc part of an immunoglobulin, a CH3 domain of an immunoglobulin, a CH4 domain of an immunoglobulin, an albumin-binding peptide, and an albumin-binding protein.

The subject in need of application of the present disclosure may be a mammal, such as a human, a dog, a mouse, a rat, a pig, an ape such as cynomolgus monkeys to name only a few illustrative examples. The term "subject" as used in the present disclosure refers to a vertebrate animal, including a mammal, and in particular a human, in which case the term "patient" can also be used.

Deregulated c-Met pathway can be induced by transcriptional up-regulation, c-Met gene amplification, specific genetic alterations, or ligand-dependent autocrine or paracrine mechanisms. The most frequent cause of constitutive c-Met activation in human tumors is increased protein expression as a consequence of transcriptional up-regulation, in the absence of gene amplification. In addition, amplification of the MET gene, with consequent protein overexpression and constitutive kinase activation, has been reported in a number of human primary tumors, including gastric and oesophageal carcinomas, non-small-cell lung (NSCL) carcinomas, and medulloblastomas. Tumors of mesenchymal origin, such as osteosarcomas and rhabdomyosarcomas, often utilize autocrine mechanisms by producing HGF. Elevated HGF levels and overexpression of c-Met are often associated with poor clinical outcomes that include more aggressive disease, increased tumor metastasis, and shortened patient survival. Further, high levels of HGF and/or c-Met proteins in tumors confer resistance to chemotherapy and radiotherapy. In addition to abnormal HGF and c-Met expression, the c-Met pathway can be activated through genetic alternations such as c-Met mutations, gene amplification, and gene rearrangement. Missense c-Met mutations are found in all individuals with well-characterized hereditary papillary renal cell carcinomas (PRCC) and in a small subset (13%) of sporadic PRCC samples. Some of the mutations possess oncogenic potential due to increased kinase activity. Trisomy of chromosome 7, where both HGF and c-Met genes reside, occurs frequently in PRCC, and results in non-random duplication of the mutant c-Met allele. In addition, somatic c-Met mutations have been identified in other human cancers, including gastric, head and neck, liver, ovarian, non-small cell lung and thyroid cancers, as well as in metastases of some of these cancers. Unlike PRCC, where mutations are typically confined to the kinase domain, these mutations are often located in other regions of the receptor, for example, the juxtamembrane domain. In addition to mutation, the c-Met gene is often amplified in breast, liver, brain, colorectal, gastric, lung and stomach cancers, which is correlated to disease progression in some patients.

Therapeutic indications aberrant HGF/c-Met signalling has been documented in a wide range of human malignancies, including bladder, breast, cervical, colorectal, endometrial, esophageal, gastric, head and neck, kidney, liver, lung, nasopharyngeal, ovarian, pancreatic, prostate and thyroid cancers, as well as cholangiocarcinoma, osteosarcoma, rhabdomyosarcoma, synovial sarcoma, Kaposi's sarcoma, leiomyosarcomas, and MFH/fibrosarcoma. In addition, abnormal HGF and/or c-Met expression has also been reported in hematological malignancies such as acute myelogenous leukemia, adult T-cell leukemia, chronic myeloid leukemia, lymphomas and multiple myeloma, as well as other tumors such as melanoma, mesothelioma, Wilms' tumor, glioblastomata, and astrocytomas (summarized in Liu et al. (2008) Expert Opin. Investig. Drugs 17(7):997-1011). The lipocalin mutein of the present disclosure can inhibit both HGF-dependent and HGF-independent tumors.

As disclosed herein, a lipocalin mutein blocks or contributes to blocking the signaling pathway of c-Met. The term "blocking the signaling pathway of c-Met", as used in the present disclosure, is hereby defined as "blocking a sufficient amount of c-Met signalling to bring about a desired therapeutic effect." This can occur, for example, by employing a c-Met antagonist lipocalin mutein to: inhibit HGF-binding to c-Met and receptor activation; induce internalization of c-Met from the cell surface in the presence or absence of HGF and also in cells comprising c-Met variants containing gain-of-function mutations; induce degradation of c-Met and reduction of phosphorylated c-Met, and thereby inhibit HGF-dependent and HGF-independent proliferation of tumor cells that express this receptor; decrease the number of available binding sites for HGF on tumor cell surfaces, and thereby terminate the pathway activation caused by overexpression, amplification, or mutation of c-Met; and block HGF-mediated c-Met phosphorylation and downstream signalling, cellular proliferation, and cellular migration.

The c-Met signalling that involves the binding of HGF to c-Met can occur, for example, when HGF induces c-Met signalling or HGF contributes to bringing about c-Met signalling. In contrast, the c-Met signalling independent of the binding of HGF to c-Met can occur, for example, when the c-Met signalling is not induced by HGF.

Because one or more lipocalin muteins of the disclosure can inhibit or contributes to inhibiting both ligand/HGF-dependent and ligand-independent c-Met pathway activation, said one or more lipocalin muteins could be therapeutically useful in treating disorders mediated by c-Met via a variety of different mechanisms.

In one preferred embodiment, the disorders mediated by c-Met can be c-Met addicted cancers and subsequent c-Met addicted metastases (Comoglio, P. M., Giordano, S. and Trusolino, L. (2008) Drug development of MET inhibitors: targeting oncogene addiction and expedience. Nat Rev Drug Discov 7: 504-516; Comoglio, P. M. and Trusolino, L. (2002) Invasive growth: from development to metastasis. J Clin Invest 109: 857-862). As used herein, the term "c-Met addicted cancer" relates to a cancer tumor that is dependent on an over-active c-Met gene for its proliferation and/or survival (Sharma, S. V. and Settleman, J. (2007) Oncogene addiction: setting the stage for molecularly targeted cancer therapy. Genes Dev 21: 3214-3231).

In yet another preferred embodiment, one or more lipocalin muteins of the disclosure can be co-administered to a subject in need thereof with one or more antagonists of HGF to treat disorders mediated by c-Met. This can be particularly applicable to treat a disorder, e.g. a cancer tumor that proliferates, as a result of both HGF-induced c-Met signaling and c-Met signaling that is independent of the binding of HGF to c-Met, whereby the co-administration of an HGF antagonist further aids in preventing HGF from inducing c-Met-signaling.

The quantitative amount of a composition that can be administered to a subject according to the present disclosure can span a wide range and frequency. For example, the amount of administered composition may be as low as 0.1 mg/kg every four weeks or as high as 50 mg/kg every second day. Preferably, the amount at each dose is selected from the group consisting of: at least 0.1 mg/kg, at least 1 mg/kg, at least 5 mg/kg, at least 10 mg/kg, at least 20 mg/kg, at least 50 mg/kg in the subject, while the frequency of administration may be selected from the group consisting of: up to twice daily, up to once daily, up to once every other day, up to once every third day, up to twice every week, up to once every week, up to once every other week and up to once every month or every two months.

The present disclosure also relates to, in the disclosed methods, using a pharmaceutical composition that includes at least one lipocalin mutein of the disclosure and, optionally, a pharmaceutically acceptable excipient.

In the disclosed methods, the pharmaceutical composition may also be administered/dosed to a subject in a variety of methods, including via any parenteral or non-parenteral (enteral) route that is therapeutically effective for proteinaceous drugs. Parenteral application methods comprise, for example, intracutaneous, intramuscular or intravenous injection and infusion techniques, e.g. in the form of injection solutions, infusion solutions or tinctures. Where administration is via intravenous infusion, the pharmaceutical composition can be administered over a period of time selected from the group consisting of: up to fifteen minutes, up to thirty minutes, up to forty-five minutes, up to one hour, up to one and half hours, up to two hours, up to two and half hours and up to three hours.

C. One or More Diagnostic Compositions of the Disclosure and Uses Thereof

To enable reliable detection of cells expressing disease-implicated levels of c-Met, the present disclosure provides a diagnostic composition for use in, e.g., an immuno-imaging technique comprising in any order: (i) a lipocalin mutein of the disclosure, or fragments, derivatives and/or combinations thereof, (ii) a half-life extending moiety and (iii) a detectable signaling label, wherein the diagnostic composition has a half-life that is needed to achieve imaging results as visualized by the detectable signaling label. In some further embodiments, the detectable signaling label is active or activatable. In some still further embodiments, the diagnostic composition further comprises a diagnostically acceptable carrier and/or excipient.

In some embodiments, as contained in a diagnostic composition of the disclosure, the lipocalin mutein as well as fragments, derivatives and/or combinations thereof, allows early detection of cells over-expressing c-Met (e.g. tumorigenic cells) on their surface because of the high affinity of the lipocalin mutein or fragments, derivatives and/or combinations thereof for c-Met. Moreover, one or more lipocalin muteins of the present disclosure as well as fragments, derivatives and/or combinations thereof, are able to be internalized within the tumorigenic cells, enabling superior imaging results (e.g. as measured by tumor-to-non-tumor ratio) and consequently a surprising sensibility and specificity for the detection of tumorigenic cells.

As shown from the disclosure herein, including data of studies as performed in the Examples, the half-life of a composition can play an important role in defining an optimal half-life that is sufficient to achieve optimal uptake yet promotes a convenient patient-administration and analysis schedule. For example, in some embodiments, the frequency of administering the diagnostic composition to a patient may be selected from the group consisting of: up to twice weekly, up to once weekly, up to once every other week, up to once every third week, up to twice every month, up to once every month, up to once every other month and up to once every three months. In this respect, a diagnostic composition of the disclosure may have a half-life within a range of about one, two, four, six, seven or fourteen days in a subject.

A diagnostic composition of the present disclosure allows the detection of c-Met expression on the surface of a cell, in a cell, in a tissue, in an organ or in a biological sample, i.e. either in vitro or in vivo, for the purpose of diagnosis, prognosis and/or post-therapy monitoring.

In some further embodiments, the present disclosure concerns a diagnostic composition of the disclosure for the detection of cells expressing c-Met. In a further embodiment of the disclosure, the detection using said diagnostic composition occurs by means of immuno-imaging techniques, such as gamma camera imaging technique/SPECT, MRI technique or PET technique. In one exemplary embodiment, the immuno-imaging technique of the disclosure may be an in vivo immuno-imaging technique.

In some embodiment, a diagnostic composition of the disclosure is suitable for use in in an immuno-imaging technique comprising gamma camera imaging technique, MRI technique or PET technique. In some embodiments, said immuno-imaging technique is an in vivo immuno-imaging technique. Various imaging procedures are available in the art to the skilled person. For example, for imaging of radioactivity, planar imaging with a gamma-camera or single photon emission computerized tomography (SPECT) can be used. In an additional example, positron emission tomography (PET) may very well be another attractive option for in vivo imaging (immuno-PET), since PET offers a high resolution and sensitivity combined with the unique ability to measure tissue concentrations of radioactivity in three dimensions.

1. Half-Life Extending Moiety

In some embodiments, a diagnostic composition of the disclosure comprises a half-life extending moiety. In some further embodiments, the half-life extending moiety of the disclosure is able to yield in a subject for the diagnostic composition a half-life compatible with the time needed to achieve imaging results as visualized by the particular detectable signaling label chosen for the diagnostic composition.

In some further embodiments, a diagnostic composition of the disclosure comprises a half-life extending moiety that can adjust the frequency of administering the diagnostic composition to a patient that is practical and convenient for the patient.

In some embodiments, one or more diagnostic compositions of the disclosure may have different half-lives, depending upon the particular half-life extending moieties utilized therein.

In some embodiments, the half-life extending moiety of the disclosure is a PEGylated moiety ranging from 5 kilo Dalton to 60 kilo Dalton or even greater. With studies as performed in the examples, the skilled can triangulate the influence of the PEG length on: (i) PK properties in subjects, and (ii) Pharmacodynamic (PD) responses (e.g. how long an lipocalin mutein of the disclosure is able to bind c-Met and/or to be internalized from the surface of cells expressing Met, at a given dose and c-Met turn-over rate. The desired half-life of a diagnostic composition of the disclosure may be different (e.g. shorter) than the desired half-life of a therapeutic composition for use in accordance with the disclosure. The desired half-life of a diagnostic composition may, for example, be hours to days, and preferably is a half-life that contributes to an in vivo imaging regimen that takes up to one or two days to complete. A particularly suitable PEG for use in accordance with the disclosure is a 20 kilo Dalton, 30 kilo Dalton or 40 kilo Dalton PEG.

In this regard, the present disclosure provides a method for selecting a diagnostic composition of the disclosure with a desired half-life, comprising: (a) administering to a first cohort of subjects a diagnostic composition containing a particular half-life-extending moiety; (b) administering to a second cohort of subjects a diagnostic composition containing a particular half-life-extending moiety that is different that the half-life-extending moiety associated with the first cohort; (c) determining the half-lives of the respective diagnostic compositions; and (d) selecting the half-life-extending moiety that is best suited for the time needed to achieve imaging results in subjects from the same or different species as the subjects in the cohorts. More than two cohorts and, hence, more than two half-life-extending moieties may be employed to determine the optimal half-life-extending moiety. The selected diagnostic composition preferably has a half-life that is practical and convenient for a patient in need thereof, such as a half-life which is no longer than necessary to achieve an accurate diagnosis or other assessment of a subject's condition related to c-Met expression.

2. Detectable Signaling Label

In some embodiments, a diagnostic composition of the disclosure suitable for use in an immuno-imaging technique comprises a suitable detectable signaling label. In some embodiments, a diagnostic composition of the disclosure comprising such detectable signaling labels permits detection or quantitation of c-Met level in a sample or subject. In some further embodiments, said detectable signaling label is detectable in vivo.

In some embodiments, the detectable signaling label of the disclosure may be already active or activatable. In some further embodiments, the detectable signaling label is activatable, for instance, by substitution with an active element, e.g. a metal, a radionuclide or a positron emitter suitable to be detected.

The detectable signaling label of the discourse can be selected, for instance, based on the immuno-imaging technique employed for the diagnosis, for example, gamma-emitting radionuclide (or gamma-emitter) in case of gamma camera-imaging technique/SPECT, metal or positron emitter in case of MRI or PET imaging techniques, respectively. In this regard, one or more detectable signaling labels of the disclosure include gamma camera-imagable agents, PET-imagable agents and MRI-imagable agents, such as, radionuclides, fluorescers, fluorogens, chromophores, chromogens, phosphorescers, chemiluminescers and bioluminescers.

In some further embodiments, a suitable detectable signaling label of the disclosure is a radionuclide. In further preferred embodiments, said radionuclide is selected from the group consisting of $^{3}$H, $^{14}$C, $^{35}$S, $^{99}$Tc, $^{123}$I, $^{125}$I, $^{131}$I, $^{m}$In, $^{97}$Ru, $^{67}$Ga, $^{68}$Ga, $^{72}$As, $^{89}$Zr and $^{201}$Tl.

In some further embodiments, a suitable detectable signaling label of the disclosure is fluorescer or fluorogen. In further preferred embodiments, said fluorescer or fluorogen is selected from the group consisting of fluorescein, rhodamine, dansyl, phycoerythrin, phycocyanin, allophycocyanin, o-phthaldehyde, fluorescamine, fluorescein derivative, Oregon Green, Rhodamine Green, Rhodol Green or Texas Red.

In some embodiments of the present disclosure, the lipocalin mutein as comprised in a diagnostic composition of the disclosure is bound to, conjugated to or labeled with one or more detectable signaling labels of the disclosure.

In some embodiments, the lipocalin mutein as comprised in a diagnostic composition of the disclosure is coupled either directly or indirectly to a detectable signaling label. In some still further embodiments, for example, the lipocalin muteins is coupled either directly (e.g. via tyrosine residues of the lipocalin mutein) or indirectly (e.g. via a linker—as a metal chelating agent) to a detectable signaling label. In some other embodiments, the lipocalin mutein is coupled to a molecule that is able to be coupled (either in vitro or in vivo) to the detectable signaling label at the time and place of use.

In some preferred embodiments, a detectable signaling label is bound to the lipocalin mutein as comprised in a diagnostic composition of the disclosure through one or more diethylenetriaminepentaacetic acid (DTPA) residues that are coupled to the lipocalin mutein.

In some embodiments, one or more diagnostic compositions of the disclosure suitable for use in MRI technique comprises a lipocalin mutein of the disclosure coupled to one or more DTPA residues, which are in turn bound to and thus labeled with one or more MRI-imagable agents. In some further embodiments, said are MRI-imagable agents are metal atoms. A number of metals can be useful for labeling in MRI technique including, for example, gadolinium, manganese, copper, iron, gold and europium. In some further preferred embodiments, gadolinium is used.

In some embodiments, when used in some of the immuno-imaging techniques (e.g. PET), the lipocalin mutein as comprised in a diagnostic composition of the disclosure may need be labeled. In some embodiments, therefore, diagnostic compositions of the disclosure may comprise one or more appropriate detectable signaling labels securely coupled (e.g. directly or through suitable chelating molecules) to the lipocalin mutein. In some still further embodiments, said detectable signaling labels have a half-life compatible with the time needed to achieve imaging results (e.g. tumor-to-non-tumor ratios).

In some embodiments where the diagnostic composition is delivered to the research/hospital site as labeled but will be used later (e.g. within 1-2 days), long-lived detectable signaling labels (e.g. positron emitters) with a half-life of 3-4 days may, for example, be used.

In some embodiments where the delivering takes about 30 hours, it is preferred to deliver the labeled diagnostic composition with 30% more radioactivity, being the quality of the conjugate well preserved up to 2 days.

In some embodiments where the delivery of the diagnostic composition takes more than 30 hours, other labeling procedures may be followed. As an example, the lipocalin mutein as comprised in a diagnostic composition of the disclosure may be delivered in a first vial as a conjugate to a suitable bi-functional chelating molecule (first conjugate) while the detectable signaling label may be delivered separately in a second vial. In some further embodiments, the detectable signaling label is ready to be coupled to the lipocalin mutein through the bi-functional chelating molecule. In such a case labeling can be easily performed at the research/hospital site of use. In addition, the first conjugate may be labeled at room temperature with the detectable signaling label at the time needed.

The present disclosure also relates to alternative procedures for labeling the lipocalin mutein as comprised in a diagnostic composition of the disclosure with a detectable signaling label, which procedures enable the storage of the diagnostic composition for a quite long period of time. In this regard, the diagnostic composition may be suitably modified but still labelled. In some further embodiments, the modified diagnostic composition can be stored until the day of use. Alternatively, the labeling may be performed immediately before use. As a preferred embodiment, the lipocalin mutein can be previously coupled to p-isothiocyanatibenzyl-desferrioxamine, which allows for subsequent coupling to the positron-emitter, e.g. $^{89}$Zr or $^{68}$Ga.

3. Industrial Applications of One or More Diagnostic Compositions of the Disclosure In some embodiments, a diagnostic composition of the disclosure can be used as a diagnostic marker or a prognostic tool in a disease or condition, where expression or enhanced expression of c-Met or c-Met's binding of HGF plays a pathological role.

In some embodiments, the present disclosure provides the use of a diagnostic composition as described herein for the manufacture of a diagnostic marker or prognostic tool for diagnosing, prognosticating, monitoring a disease or condition in a subject, wherein expression or enhanced expression of c-Met or c-Met's binding of HGF plays a pathological role. In some further embodiments, said disease or condition is a cancer or a tumor.

A diagnostic composition of the present disclosure may be used in diagnostic, prognostic, monitoring or research procedures in conjunction with any appropriate cell, tissue, organ or biological sample of one or more subjects, for example, humans (e.g. patients) as well as the desired animal species. By the term "biological sample" is intended any fluid or other material derived from the body of a normal or diseased subject, such as blood, serum, plasma, lymph, urine, saliva, tears, cerebrospinal fluid, milk, amniotic fluid, bile, ascites fluid, pus and the like. Also included within the meaning of this term is an organ or tissue extract and a culture fluid in which any cells or tissue preparation from the subject that has been incubated. By the term "subject" is intended any vertebrate animal, including any mammal, such as a human (in which case the term "patient" can also be used), a dog, a mouse, a rat, a pig, an ape such as cynomolgus monkeys to name only a few illustrative examples.

In some embodiments, the present disclosure provides a method for detecting abnormal levels of c-Met on the surface of a cell, in a cell, in a tissue, in an organ or in a biological sample of a subject, which cell, tissue, organ or sample is suspected of over-expressing c-Met vis-à-vis normal physiological conditions in the subject, comprising the steps of: (a) contacting the cell, tissue, organ or sample with a diagnostic composition of the disclosure and (b) determining whether the organ or the biological sample over-expresses c-Met by quantifying the level of c-met via the detectable signaling label associated with the diagnostic composition.

In some embodiments, the present disclosure provides a method to locate the c-Met-over-expressing cells, tissue or organ in a subject, comprising the steps of: (a) contacting the cell, tissue, organ with a diagnostic composition of the disclosure; (b) detecting the presence of the detectable signaling label associated with the cell, tissue, organ or sample by means of an immuno-imaging technique of the disclosure; and (c) quantifying the level of c-met thereby.

In some embodiments, the present disclosure provides a method of determining the progression or regression of c-Met-expressing cancer or tumor in a subject having cancer or tumor, comprising the steps of: (a) contacting a biological sample taken from the subject with one or more diagnostic compositions of the disclosure; (b) measuring the amount of the detectable signaling label(s) associated the sample with by means of an immuno-imaging technique of the disclosure; and (c) correlating the amount of the detectable signaling labels associated the sample with the amount of c-Met in the subject. In this respect, the increased amount of detectable signaling label(s) in the sample taken from the subject relative to the amount of detectable signaling label(s) in a control sample indicates an increased amount of c-Met in the subject, and the increased amount of Met in the subject in turn suggests the progression of c-Met-expressing cancer or tumor in the subject; in contrast, the decreased amount of detectable signaling label(s) in the sample taken from the subject relative to the amount of detectable signaling label(s) in a control sample indicates an decreased amount of c-Met in the subject, and the decreased amount of Met in the subject in turn suggests the regression of c-Met-expressing cancer or tumor in the subject.

In above said methods, the contacting and the detecting may be in vitro; the contacting may be in vivo while the detecting may be in vitro, or, in some embodiments, the contacting and the detecting are both in vivo. The methods may be carried out for purposes of diagnosis, prognosis, and/or monitoring (e.g., post-therapy). In some embodiments, the present disclosure provides a method for the in vivo detection of c-Met-over-expressing cell, tissue or organ in a subject by means of an immuno-imaging technique comprising administering to said subject a diagnostic composition of the disclosure. In some further embodiments, the in vivo detection is by a radionuclide, and in some preferred embodiments, by radioimmunoscintigraphy.

In some embodiments, the immuno-imaging technique as used in above said methods comprises gamma camera imaging technique, MRI technique or PET technique. In some embodiments, the immuno-imaging technique as used in said method comprises gamma camera imaging technique, MRI technique or PET technique, and wherein the detectable signaling label may be a gamma camera-imagable agent, a PET-imagable agent, and a MRI-imagable agent, respectively.

In above said methods, the frequency of contacting the cell, tissue, organ or sample with one or more diagnostic compositions of the disclosure or of administering said composition to a subject can be adjusted, for example, by using different serum half-life extending moieties.

Generally, the amount of diagnostic compositions of the disclosure needed for detectability in all above-mentioned methods will vary depending on considerations such as age, condition, sex, and extent of disease in the patient, contraindications, if any, and other variables, and is to be adjusted by the individual physician or diagnostician. For in vivo applications, dosage can vary from 0.01 mg to 100 mg of each single diagnostic composition or combination of diagnostic compositions, and preferably is within a range of 5 to 50 mg.

In some embodiments, above said methods using diagnostic compositions of the disclosure may utilize gamma camera-imaging technique, wherein the methods comprise a detectable label that is a gamma camera-imagable agent of the disclosure.

In some embodiments, above said methods using diagnostic compositions of the disclosure may utilize MRI imaging technique, wherein the methods comprise a detectable label that is a MRI-imagable agent of the disclosure.

In some embodiments, above said methods using diagnostic compositions of the disclosure may utilize PET imaging technique, wherein the methods comprise a detectable label that is a PET-imagable agent of the disclosure.

The procedures for production, purification of large amounts of these positron emitters and for their stable coupling to lipocalin muteins of the disclosure, with maintenance of the in vivo biodistribution characteristics of the latter, are known in the art (see Verel I, et al., Eur J Nucl Med Mol Imaging 2004; 31:1645-52 and Verel I, et al., J Nucl Med 2003; 44:1271-81).

In some further embodiments, long-lived positron emitters, the residualizing radionuclide $^{89}$Zr and the non-residualizing radionuclide $^{124}$I, can be utilized for PET imaging with lipocalin muteins of the disclosure in above said methods. In some embodiments, $^{89}$Zr can be coupled via a chelate to the lysine residues of lipocalin muteins. In some embodiments, $^{124}$I can be coupled directly via tyrosine residues. In some preferred embodiments, $^{89}$Zr is used for PET imaging of internalizing lipocalin muteins. In some preferred embodiments, $^{124}$I is used for non-internalizing lipocalin muteins. Because, in contrast to directly labeled $^{124}$I, $^{89}$Zr is trapped in the cell after internalization of the lipocalin muteins, which is known in the art as residualization (Borjesson et al., Clin Cancer Res 2006; 12: 3133-40). In addition, residualization of sup.89Zr can occur in organs associated with lipocalin muteins catabolism, such as liver, kidney and spleen.

In some preferred embodiments, the residualizing radionuclide such as $^{89}$Zr is better suited for PET imaging with lipocalin muteins that can be internalized after binding to the cell than non-residualizing iodine such as $^{124}$I. In some other preferred embodiments, non-residualizing iodine is also used for PET imaging with lipocalin muteins that can be internalized after binding to the cell, for example, when indirect radio-iodination methodologies are applied to result in higher retention of radioactivity in tumour cells after the internalization of labeled lipocalin muteins.

In some further embodiments, residualizing radionuclide (e.g. $^{89}$Zr)-immuno-PET can be used for non-invasive quantification of biodistribution of lipocalin muteins. In some preferred embodiments, quantitative PET imaging would be preferable over repeated tumor biopsies, especially because tumors are often heterogeneous (resulting in non-representative biopsies) and difficult accessible.

In some embodiments, the present disclosure provides a diagnostic composition as described herein for use in any of the methods mentioned above for the purpose of detection of the presence of c-Met. In some embodiments, the present disclosure provides a diagnostic composition as described herein for use in any of the methods mentioned above for the purposes of diagnosis, prognosis, and/or monitoring (e.g., post-therapy) of a disease or condition, wherein expression or enhanced expression of Met or Met's binding of HGF plays a pathological role.

In some embodiments, the present disclosure provides a diagnostic kit comprising at least one diagnostic composition of the disclosure and one or more instructions for using the diagnostic composition, for diagnosing, prognosticating, monitoring a disease or condition (e.g. a cancerous condition or a tumor) in a subject, wherein expression or enhanced expression of c-Met or Met's binding of HGF plays a pathological role. In a still further embodiment, the diagnostic composition can be internalized from the surface of cells expressing c-Met following the binding of said composition to a c-Met molecule on the cell surface.

In some further embodiments, the present disclosure provides a diagnostic kit comprising at least one diagnostic composition of the disclosure and one or more instructions for using the diagnostic composition, for measuring whether c-Met is over-expressed in one or more biological samples taken from a subject, as compared to one or more normal control samples. The kit may contain: a labeled first container comprising at least one diagnostic composition of the disclosure; a labeled second container comprising a diagnostically acceptable carrier or excipient; and instructions for using the kit to diagnose, prognosticate, or monitor said disease or condition in a subject.

All patents, patent applications, text books and peer-reviewed publications described herein are hereby incorporated by reference in their entirety.

The following non-limiting examples illustrate various aspects of the present disclosure.

EXAMPLES

Example 1

The Evaluation of Anti-Tumour Effects of a Lipocalin Mutein (SEQ ID NO: 1) in the Caki-1 Xenograft Model Mice were implanted subcutaneously (s.c.) with 100 µl of 5×106 Caki-1 cells in the right flank at the beginning of the study. All the mice were observed every day to monitor the health and tumor size. When tumors reached an average volume of 100-150 mm3, 80 out of the 96 mice were selected based on their tumor volume and randomly assigned to efficacy groups prior to dosing. Each group consisted of 10 tumor-bearing mice (n=10/group). Tumor-bearing mice in treatment groups were treated (daily intraperitonealy (i.p.)) with vehicle, TLC control-PEG40 (30 mg/kg) and the lipocalin mutein (30 mg/kg, 15 mg/kg, 7.5 mg/kg, 2.5 mg/kg, and 0.75 mg/kg), starting on the day after randomization. Mice were weighed at each dosing and recorded every day. FIG. 1 shows the tumor-growth inhibition of the lipocalin mutein (30 mg/kg, 15 mg/kg, 7.5 mg/kg, 2.5 mg/kg and 0.75 mg/kg) groups in the Caki-1 xenograft tumor model. Statistically significant reduction of tumor volumes was observed in each of the lipocalin mutein treatment groups when compared with vehicle group and TLC control.

Example 2

Analysis of Body Weight Change as an Index of In Vivo Safety (Tolerability) of a lipocalin Mutein (SEQ ID NO: 1)

Figure 2:
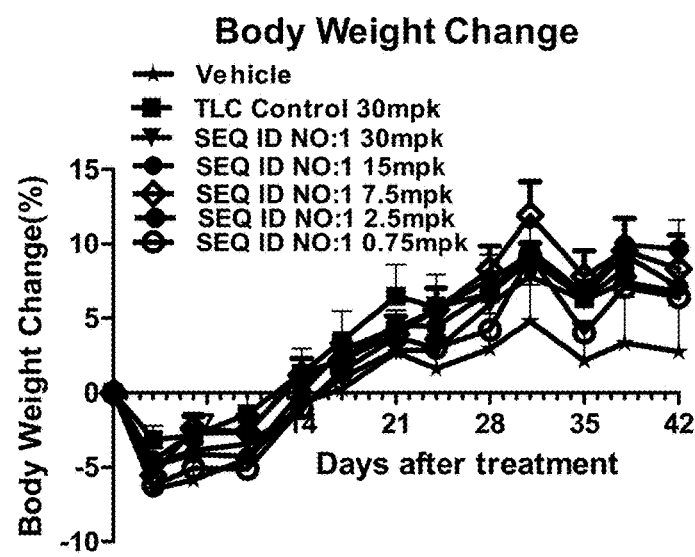
FIG. 2 shows the percentage (%) weight change in each study group. All groups suffered similar levels of body weight loss in the first week of treatment (likely due to adaptive stress) but subsequently gained weight through the study. No signs of toxicity were observed. There was no difference in body weight patterns between the vehicle control group and the lipocalin mutein (SEQ ID NO: 1) groups, suggesting that the compound is well tolerated at all dose levels tested.

The body weights of Caki-1 tumor-bearing nude mice were monitored for fluctuations due to administration of test compounds including the lipocalin mutein (SEQ ID NO: 1). Tumor-bearing mice were treated (daily intraperitonealy (i.p.)) with vehicle, TLC control-PEG40 (30 mg/kg) and the lipocalin mutein (30 mg/kg, 15 mg/kg, 7.5 mg/kg, 2.5 mg/kg, and 0.75 mg/kg). Body weights were recorded daily and all mice were monitored for signs of toxicity. All groups suffered similar levels of body weight loss in the first week of treatment (likely due to adaptive stress) but subsequently gained weight through the study. No signs of toxicity were observed. As shown in FIG. 2, there was no difference in body weight patterns between the vehicle control group and the lipocalin mutein groups, suggesting that the compound is well tolerated at all dose levels tested.

Example 3

Determination of the Effect of a Lipocalin Mutein (SEQ ID NO: 1) on Total Met Receptor Expression and Met Phosphorylation (Signaling) in the Caki-1 and EBC-1 (Ligand Independent Models)

Figure 3:
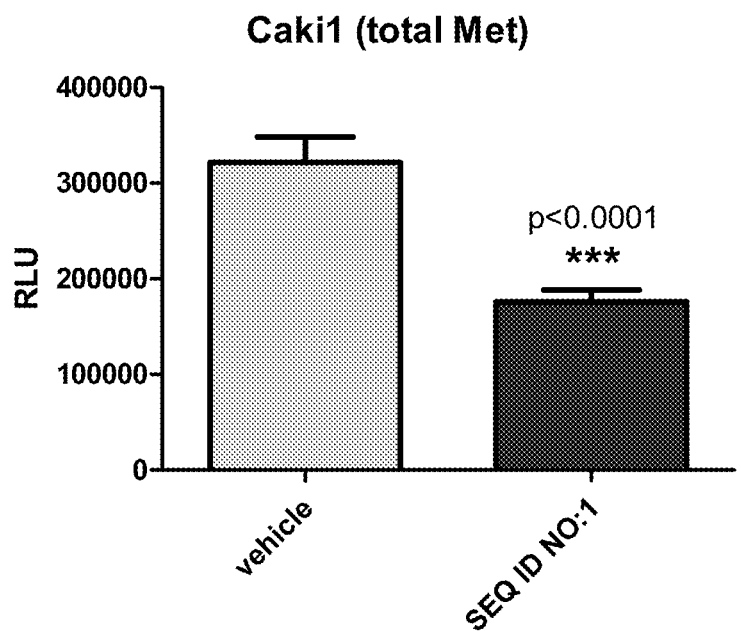
FIG. 3 shows the changes in total Met and phosphorylated Met expression in both Caki-1 and EBC-1 xenograft tumor biopsies after 5 days treatment with the lipocalin mutein (SEQ ID NO: 1) (7.5 mg/kg) or control. Total Met expression levels were significantly reduced following treatment with the lipocalin mutein (SEQ ID NO: 1). Treatment with the lipocalin mutein (SEQ ID NO: 1) also led to a significant reduction in the level of phosphorylated Met.
Figure 3:
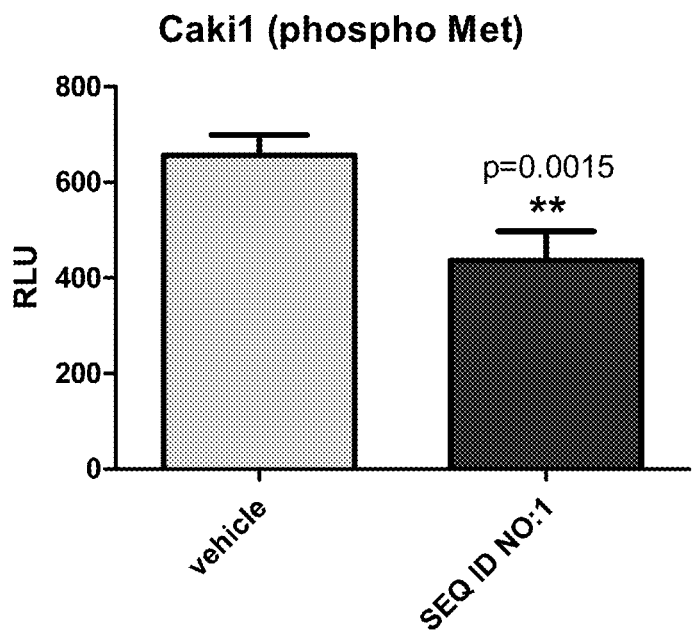
Figure 3:
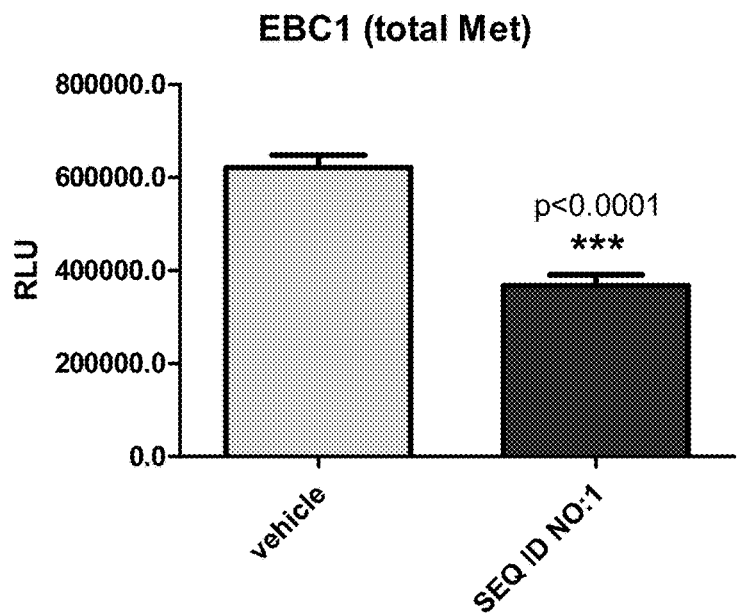
Figure 3:
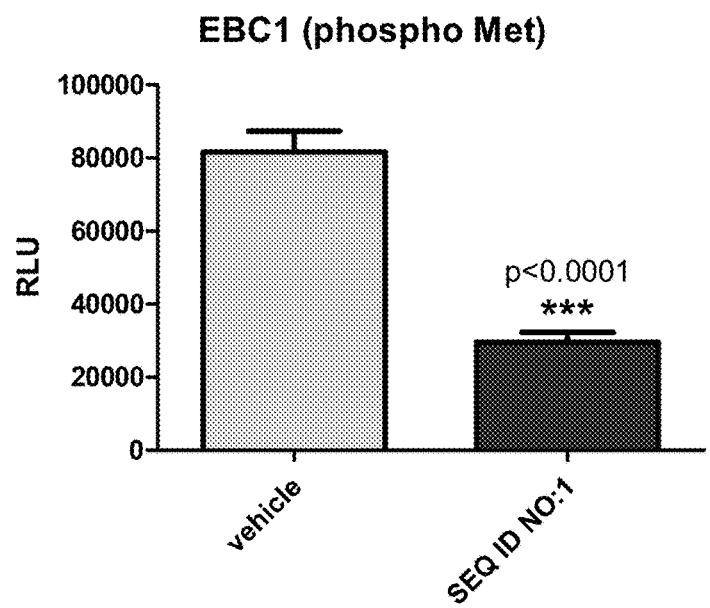

ELISA-based quantification of phosphorylated Met and total Met was performed on tumor tissues excised from Caki-1 and EBC-1 cell xenograft models following 5 days treatment with vehicle or the lipocalin mutein (SEQ ID NO: 1). It was demonstrated in FIG. 3 that the lipocalin mutein significantly reduces phosphorylated Met and total endogenous c-Met in both ligand independent Caki-1 and EBC-1 cell xenograft models (P<0.01).

Example 4

Figure 4:
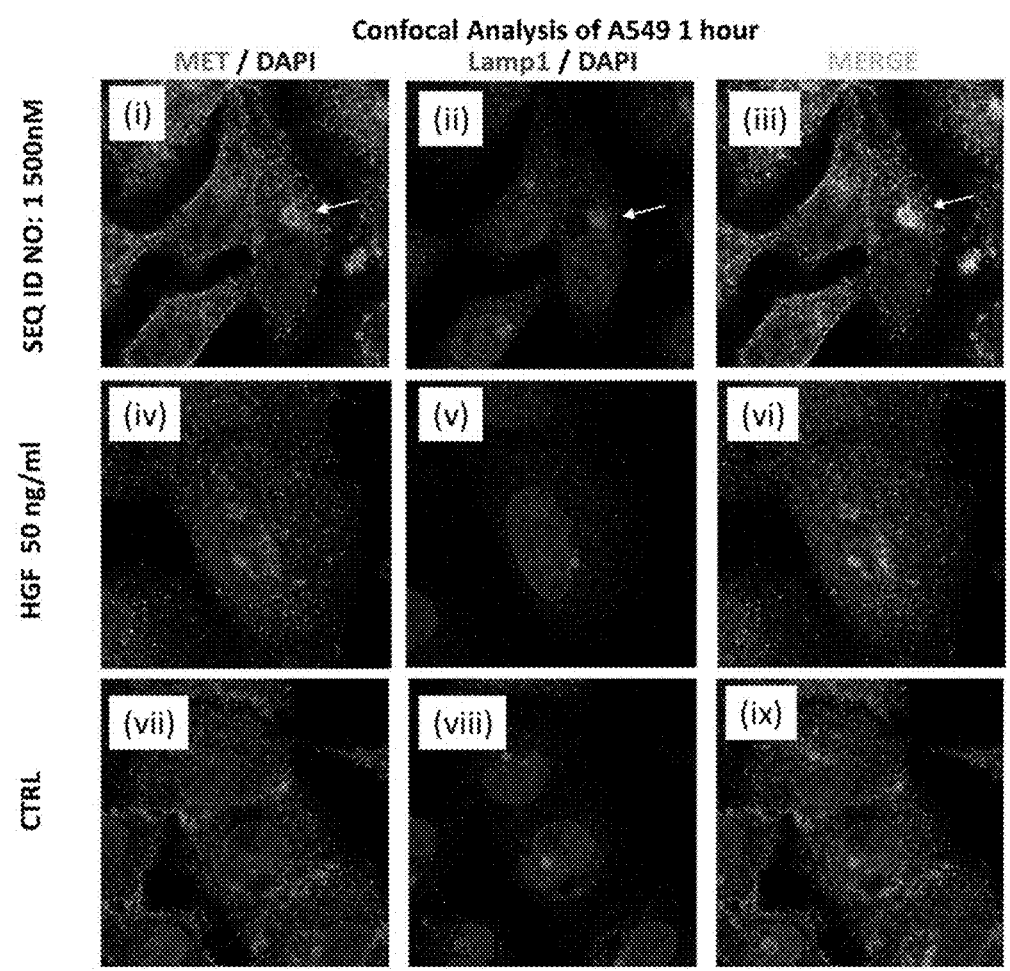
FIG. 4 shows the impact of the lipocalin mutein (SEQ ID NO: 1) on c-Met receptor in A549 cells. Immunofluorescence staining shows treatment with SEQ ID NO: 1 leads to accumulation of c-Met in LAMP-1 positive vesicles indicating receptor degradation.

Determination of the Effect of a Lipocalin Mutein (SEQ ID NO: 1) on Total Met Receptor Expression in the A549 and Caki-1 Cell Line Model Immunofluorescence microscopy was performed on A549 cells to assess faith of c-Met receptor upon exposure to the lipocalin mutein (SEQ ID NO: 1). A549 cells plated on glass coverslips were incubated for with SEQ ID NO: 1 (500 nM) or HGF (50 ng/ml, from R&D Systems, Minneapolis, Minn.) or control medium for 1 hour on ice followed by 1 hr at 37° C. to allow internalization. Cells were then fixed in 4% para-formaldehyde and permeabilized to facilitate staining with primary antibodies (anti-Met recognizing the c-terminal tail of the Met receptor: mouse mAb 3D4 from Invitrogen, Camarillo, Calif.; anti-LAMP-1 cat. # L1418: rabbit polyclonal antibody from Sigma Life Science), prior to incubation with appropriate Alexa-Fluor-tagged secondary antibodies (Molecular Probes by Life Technologies, Karlsruhe, Germany). Nuclei were counterstained blue with DAPI (This is visualized as a large blue circle within each cell which aids single-cell analysis). Immunofluorescence was analyzed using a Leica TCS SP2 AOBS confocal laser-scanning microscope (Leica Microsystems). The impact of SEQ ID NO: 1 on c-Met was evident by the accumulation of the receptor in intracellular compartments. FIG. 4 image (i) shows the highest signal intensity of Met receptor staining (in green) localising to intracellular vessicles following incubation with SEQ ID NO: 1 (when compared to control panels in FIG. 4 image iv and vii). Counterstaining with LAMP-1 (red) demonstrates a colocalisation (yellow) of c-Met receptor with a terminal endolysosomal vesicle when exposed to SEQ ID NO: 1 as shown in FIG. 4 image (iii) indicating its degradation. Immunoflourescent microscopy also demonstrated removal of c-Met from the cell surface in Caki-1 cells in response to SEQ ID NO: 1. Cells grown in 8 chamber glass slides were incubated with test substance and c-Met expression pattern was assessed using rabbit monoclonal c-Met (C-12) (Santa Cruz, sc-10). Confocal images were used to determine relative intensity values of fluorescent signal coming from plasma membrane localized c-met receptor. High magnifications of images were used to draw 15 pixel wide regions of interest (ROI) over border of imaged cells (imageJ software). Mean intensity of the pixels within the same ROI was then assessed in corresponding single channel fluorescent images from independent experiments. A significant reduction in pixel intensity was observed in the SEQ ID NO: 1 treated samples relative to controls.

Example 5

Determination of Internalisation of a Lipocalin Mutein (SEQ ID NO: 1) Upon Binding c-Met Receptor in the H441 and A549 Cell Line Models Immunofluorescence microscopy was performed on A549 cells to assess internalisation of the lipocalin mutein (SEQ ID NO: 1). A549 cells plated on glass coverslips were incubated for with SEQ ID NO: 1 DyLight$^{633}$ (500 nM) for 1 hour on ice. Cells were then incubated for 1 hr at 37° C. to allow internalization. Nuclei were counterstained blue with DAPI (This is visualized as a large blue circle within each cell which aids single-cell analysis). Immunofluorescence was analyzed using a Leica TCS SP2 AOBS confocal laser-scanning microscope (Leica Microsystems). It was demonstrated that the lipocalin mutein (SEQ ID NO: 1) binds to c-Met receptor and is internalised as shown by the intense pink intracellular staining observed in FIG. 5 A.

Figure 5:
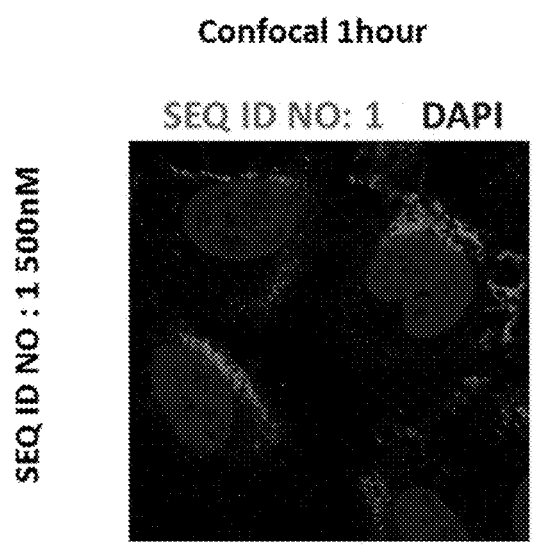
FIG. 5 shows internalization of SEQ ID NO: 1 upon binding in A549 and H441 cell line models. Immunofluorescence microscopy of A549 cells show intracellular accumulation of fluorescently labeled SEQ ID NO: 1. Radioactivity measurements of cell surface, intracellular and supernatant fractions of H441 cells exposed to radiolabelled lipocalin mutein demonstrate membrane binding and internalization of $^{89}$Zr-SEQ ID NO: 1.
Figure 5:
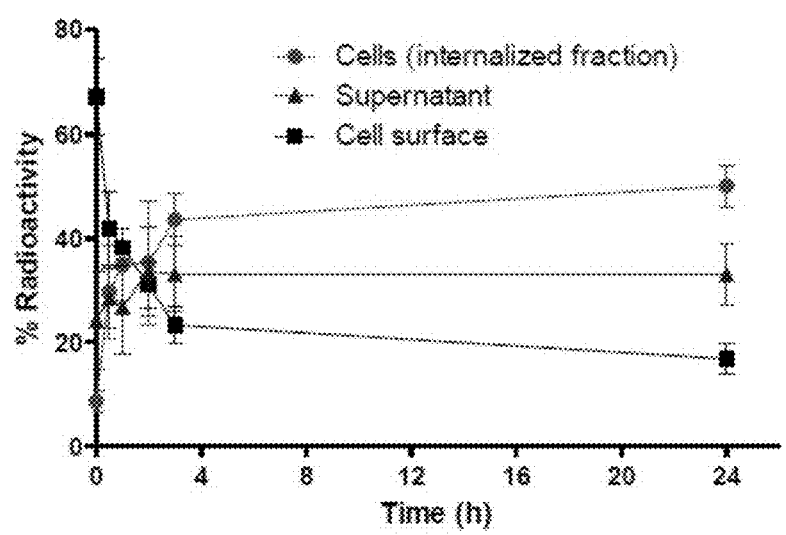

To further assess the internalisation kinetics of the lipocalin mutein (SEQ ID NO: 1) H441 cells were incubated on ice with 0.1 µg of radiolabelled lipocalin mutein, $^{89}$Zr-SEQ ID NO: 1, for 1.5 h to allow binding. After washing cells were incubated at 37° C. to allow for internalization. Internalized, membrane bound and $^{89}$Zr-RS-110 released in the medium was counted in a LKB-1282-Compu-gamma system (LKB Wallac). $^{89}$Zr-SEQ ID NO: 1 was rapidly internalized (FIG. 5 B). The internalized fraction increased from 3 h after start of incubation and stabilized thereafter up to 24 h. Cell surface $^{89}$Zr-SEQ ID NO: 1 decreased during this period.

Example 6

Demonstration of Tumor Specific Uptake of $^{89}$Zr-SEQ ID NO: 1

Figure 6:
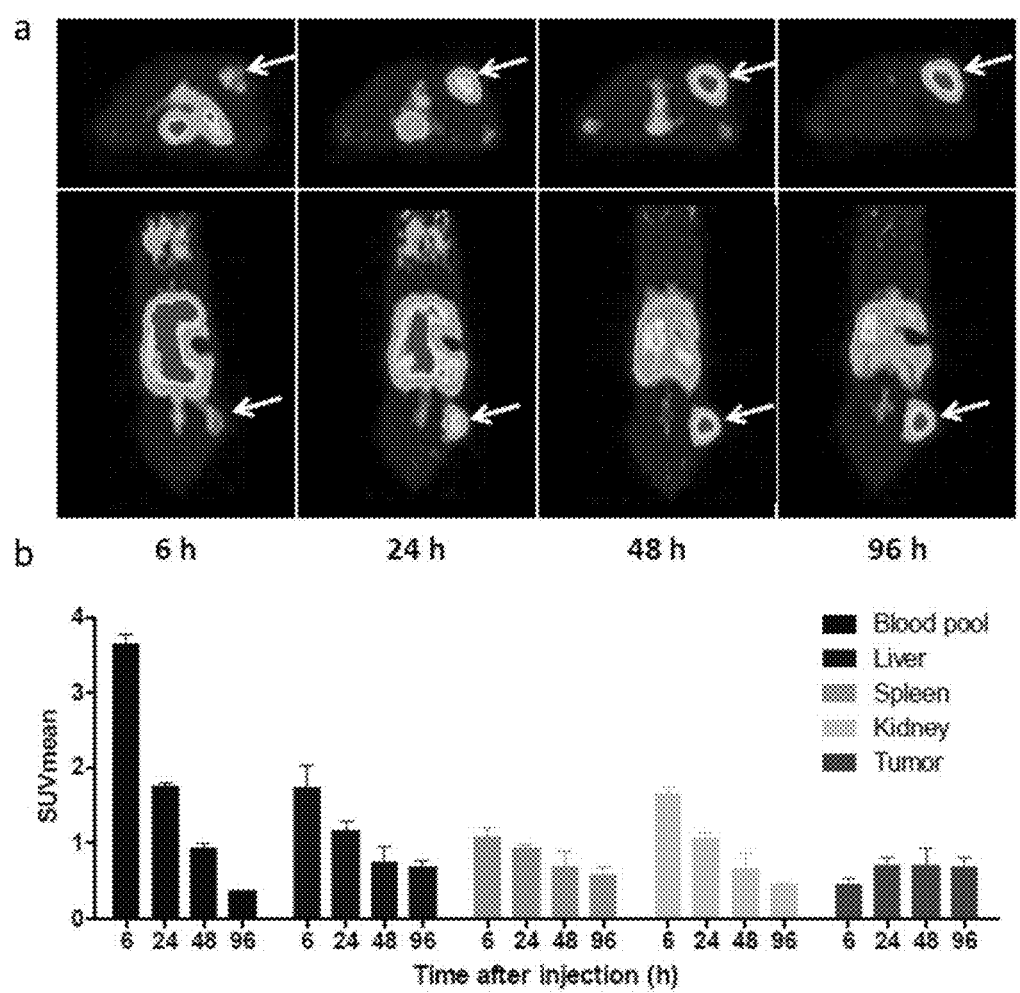
FIG. 6 shows $^{89}$Zr-SEQ ID NO: 1 microPET imaging of H441 bearing mice. Representative transversal and coronal microPET images are shown at 6, 24, 48 and 96 h after tracer injection (a). MicroPET data quantification was performed for blood pool, liver, spleen, kidney and tumor uptake in all mice (b). Data are expressed as the mean standardized uptake value (SUVmean).
Figure 7:
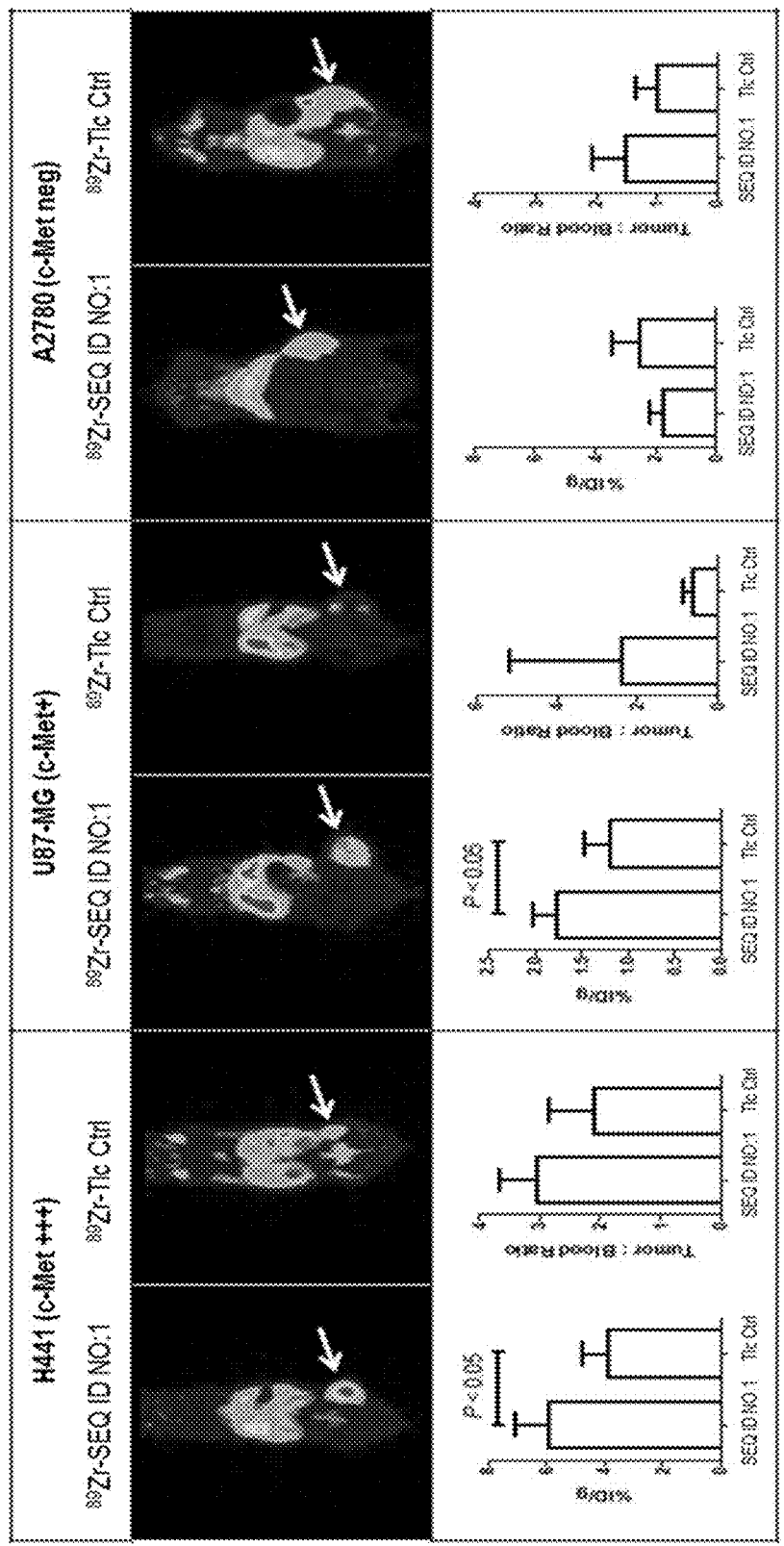
FIG. 7 shows $^{89}$Zr-SEQ ID NO: 1 microPET imaging of H441, U87-MG and A2780 bearing mice. Representative transversal and coronal microPET images are shown at 96 h after tracer injection of $^{89}$Zr-SEQ ID NO: 1 for c-Met driven tumor uptake and $^{89}$Zr-Tlc ctrl for non-specific tumor uptake. Ex vivo tumor uptake of $^{89}$Zr-SEQ ID NO: 1 and $^{89}$Zr-Tlc ctrl. To compare specific tumor uptake between tumor models, tumor:blood ratios are provided.

MicroPET imaging of H441 tumor bearing mice was used to assess tumor specific uptake and time dependent organ distribution of $^{89}$Zr-SEQ ID NO: 1. Animals were imaged using a microPET Focus 220 rodent scanner (CTI Siemens). After image reconstruction, in vivo quantification was performed with AMIDE Medical Image Data Examiner software (version 0.9.1, Stanford University). Samples and primed standards were counted for radioactivity in a well-type gamma-counter and corrected for physical decay. Ex vivo tissue activity is expressed as percentage of the injected dose per gram tissue (% ID/g). Representative transversal and coronal microPET images are shown at 6, 24, 48 and 96 h in FIG. 6 (A) after tracer injection (50 µg $^{89}$Zr-SEQ ID NO: 1 (5 MBq)) with white arrow indicating tumor uptake. Tumor uptake increased between 6 and 24 h. MicroPET data quantification was performed for blood pool, liver, spleen, kidney and tumor uptake in all mice. MicroPET scan analysis of non-target tissues in xenograft mice revealed a high blood pool, together with liver and kidney tracer uptake, 6 h after injection of 50 µg $^{89}$Zr-SEQ ID NO: 1. The non-specific uptake in these organs decreased over time based on the scans performed at 24, 48 and 96 h after injection resulting in increased tumor:organ ratios up to 96 h after tracer injection (FIG. 6 B). Specific c-Met directed uptake was also seen in H441 and U87-MG tumors compared to $^{89}$Zr-Tlc ctrl (FIG. 7). A2780 xenografts (c-Met negative) showed background non-specific tumor uptake of both $^{89}$Zr-SEQ ID and $^{89}$Zr-Tlc ctrl, Data are expressed as the mean standardized uptake value (SUVmean).

After the last scan, mice were sacrificed for biodistribution analysis. Biodistribution data was fully consistent with the microPET findings, showing ex vivo tumor uptake of $^{89}$Zr-SEQ ID correlated with c-Met expression (5.9% ID/g in H441 and 1.8% ID/g in U87-MG) (P<0.05) (FIG. 7). $^{89}$Zr-Tlc ctrl control tracer tumor uptake in these models was 3.9 (H441), 1.2 (U87-MG) and 2.5 (A2780) % ID/g. No difference was found between $^{89}$Zr-Tlc ctrl (1.7% ID/g) and $^{89}$Zr-Tlc ctrl (2.5% ID/g) tumor uptake in the A2780 (c-Met negative) model. Tumor:blood ratios of $^{89}$Zr-SEQ ID compared to $^{89}$Zr-Tlc ctrl confirmed these finding.

---

The invention claimed is:

1. A lipocalin mutein having at least 95% sequence identity to the amino acid sequence set forth in SEQ ID NO: 1 or SEQ ID NO: 2, wherein sequence identity is determined by dividing the number of identical residues by the total number of residues and multiplying the product by 100, wherein said mutein is capable of inducing internalization of c-Met from the surface of a cell that expresses c-Met, and wherein the mutein comprises, at positions 26-34, 56-58, 80, 83, 104-106, and 108 corresponding to the linear polypeptide sequence of the mature human tear lipocalin (SEQ ID NO: 3), the same set of amino acid residues that the muteins set forth in SEQ ID NO: 1 or SEQ ID NO: 2 have at the respective positions.

2. The mutein of claim 1, wherein the mutein is conjugated to a compound that extends the serum half-life of the mutein, wherein compound is selected from the group consisting of a polyalkylene glycol molecule, a hydroxyethyl starch, a protein domain, a Fc part of an immunoglobulin, a CH3 domain of an immunoglobulin, a CH4 domain of an immunoglobulin, an albumin-binding peptide, and an albumin-binding protein.

3. The mutein of claim 1, wherein the mutein lacks at least one N-terminal or C-terminal amino acid of SEQ ID NO: 1 or SEQ ID NO: 2.

4. A pharmaceutical composition comprising the mutein of claim 1.

5. The pharmaceutical composition of claim 4, which is formulated for parenteral administration.

6. The pharmaceutical composition of claim 4, which is formulated for enteral administration.

7. The mutein of claim 1, wherein the mutein comprises the amino acid sequence set forth in SEQ ID NO: 1 or SEQ ID NO: 2.

8. The mutein of claim 1, wherein the mutein comprises the amino acid sequence set forth in SEQ ID NO: 1 or SEQ ID NO: 2 except the first four N-terminal amino acid residues and the last two C-terminal amino acid residues.

* * * * *

SEQUENCE LISTING

```
<160> NUMBER OF SEQ ID NOS: 3

<210> SEQ ID NO 1
<211> LENGTH: 158
<212> TYPE: PRT
<213> ORGANISM: Artificial
<220> FEATURE:
<223> OTHER INFORMATION: Mutein of human tear lipocalin

<400> SEQUENCE: 1

Leu Leu His His Ala Ser Asp Glu Glu Ile Gln Asp Val Ser Gly Thr
1               5                   10                  15

Trp Tyr Leu Lys Ala Met Thr Val Asp Thr Gln Asp Pro Leu Ser Leu
            20                  25                  30

Tyr Val Ser Val Ser Pro Ile Thr Leu Thr Thr Leu Glu Gly Gly Asn
        35                  40                  45

Leu Glu Ala Thr Val Thr Leu Asn Gln Ile Gly Arg Ser Gln Glu Val
    50                  55                  60

Leu Ala Val Leu Glu Lys Thr Asp Glu Pro Gly Lys Tyr Thr Leu Tyr
65                  70                  75                  80

Gly Gly Ala His Val Ala Tyr Ile Gln Arg Ser His Val Lys Asp His
                85                  90                  95

Tyr Ile Phe Tyr Ser Glu Gly Asp Thr Trp Gly Gly Pro Val Pro Gly
            100                 105                 110

Val Trp Leu Val Gly Arg Asp Pro Lys Asn Cys Leu Glu Ala Leu Glu
        115                 120                 125
```

```
Asp Phe Glu Lys Ala Ala Gly Ala Arg Gly Leu Ser Thr Glu Ser Ile
            130                 135                 140

Leu Ile Pro Arg Gln Ser Glu Thr Ser Ser Pro Gly Ser Asp
145                 150                 155
```

<210> SEQ ID NO 2
<211> LENGTH: 158
<212> TYPE: PRT
<213> ORGANISM: Artificial
<220> FEATURE:
<223> OTHER INFORMATION: Mutein of human tear lipocalin

<400> SEQUENCE: 2

```
Leu Leu His His Ala Ser Asp Glu Glu Ile Gln Asp Val Ser Gly Thr
1               5                   10                  15

Trp Tyr Leu Lys Ala Met Thr Val Asp Thr Gln Asp Pro Leu Ser Leu
            20                  25                  30

Tyr Val Ser Val Ser Pro Ile Thr Leu Thr Thr Leu Glu Gly Gly Asn
            35                  40                  45

Leu Glu Ala Thr Val Thr Leu Asn Gln Ile Gly Arg Ser Gln Glu Val
        50                  55                  60

Leu Ala Val Leu Glu Lys Thr Asp Glu Pro Gly Lys Tyr Thr Leu Tyr
65                  70                  75                  80

Gly Gly Ala His Val Ala Tyr Ile Gln Arg Ser His Val Lys Asp His
                85                  90                  95

Tyr Ile Phe Tyr Ser Glu Gly Asp Thr Trp Gly Gly Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
            130                 135                 140

Leu Ile Pro Arg Gln Ser Glu Thr Ser Ser Pro Gly Ser Asp
145                 150                 155
```

<210> SEQ ID NO 3
<211> LENGTH: 158
<212> TYPE: PRT
<213> ORGANISM: human
<220> FEATURE:
<223> OTHER INFORMATION: Human tear lipocalin

<400> SEQUENCE: 3

```
His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
            20                  25                  30

Leu Glu Ser Val Thr Pro Met Thr Leu Thr Thr Leu Glu Gly Gly Asn
            35                  40                  45

Leu Glu Ala Lys Val Thr Met Leu Ile Ser Gly Arg Cys Gln Glu Val
        50                  55                  60

Lys Ala Val Leu Glu Lys Thr Asp Glu Pro Gly Lys Tyr Thr Ala Asp
65                  70                  75                  80

Gly Gly Lys His Val Ala Tyr Ile Ile Arg Ser His Val Lys Asp His
                85                  90                  95

Tyr Ile Phe Tyr Cys Glu Gly Glu Leu His Gly Lys Pro Val Arg Gly
            100                 105                 110

Val Lys Leu Val Gly Arg Asp Pro Lys Asn Asn Leu Glu Ala Leu Glu
        115                 120                 125
```

```
Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145             150                 155
```